United States Patent [19]

Fuhr et al.

[11] Patent Number: 5,925,511
[45] Date of Patent: Jul. 20, 1999

[54] CRYOPRESERVING AND CRYOGENICALLY PROCESSING BIOLOGICAL OBJECTS

[75] Inventors: Günter Fuhr; Jan Hornung; Rolf Hagedorn; Torsten Müller, all of Berlin; Steffen Howitz, Dresden; Bernd Wagner, Looft; Ulrich Hofmann, Itzehoe, all of Germany

[73] Assignee: Fraunhofer Gesellschaft Zur Fordereung Der Angeweandten Forschung E.V., Munich, Germany

[21] Appl. No.: 08/836,092

[22] PCT Filed: Oct. 26, 1995

[86] PCT No.: PCT/DE95/01490

§ 371 Date: Aug. 29, 1997

§ 102(e) Date: Aug. 29, 1997

[87] PCT Pub. No.: WO96/13159

PCT Pub. Date: May 9, 1996

[30] Foreign Application Priority Data

Oct. 26, 1994 [DE] Germany ............... P 44 38 232

[51] Int. Cl.$^6$ ...................................... A01N 1/02
[52] U.S. Cl. ............... 435/1.3; 435/40.5; 435/284.1; 435/286.4; 435/287.3; 435/288.7
[58] Field of Search ................ 435/1.3, 40.5, 435/40.51, 284.1, 286.2, 286.4, 287.1, 287.3, 288.7; 62/63, 65, 78

[56] References Cited

U.S. PATENT DOCUMENTS

| | | |
|---|---|---|
| 4,142,656 | 3/1979 | Smith et al. ................ 222/325 |
| 4,399,219 | 8/1983 | Weaver ........................ 435/34 |
| 4,531,373 | 7/1985 | Rubinsky ..................... 62/63 |
| 4,578,963 | 4/1986 | Sitte .......................... 62/514 |
| 4,580,416 | 4/1986 | Sitte .......................... 62/514 R |
| 5,108,926 | 4/1992 | Klebe ......................... 435/284 |
| 5,132,089 | 7/1992 | Lightfoot .................... 422/99 |
| 5,780,295 | 7/1998 | Livesey et al. ............... 435/307.1 |

FOREIGN PATENT DOCUMENTS

| | | | |
|---|---|---|---|
| 0 331 855 A2 | 9/1989 | European Pat. Off. . | |
| 0 397 413 A1 | 11/1990 | European Pat. Off. | C12M 3/00 |
| 0 475 409 A2 | 3/1992 | European Pat. Off. | A01N 1/02 |
| 2 651 793 | 3/1991 | France . | |
| 1708835 | 1/1992 | U.S.S.R. . | |
| WO 82/02562 | 8/1982 | WIPO | C12Q 1/18 |
| WO 93/03493 | 2/1993 | WIPO | H01J 41/04 |
| WO 93/22598 | 11/1993 | WIPO | F17C 7/04 |

*Primary Examiner*—David A. Redding
*Attorney, Agent, or Firm*—William H. Murray; N. Stephan Kinsella

[57] ABSTRACT

For the fixated cryopreservation of single living biological objects or such objects compiled in a given number (for example cells) a cryogenically cooled substrate (13) is jetted therewith in a enveloping solution in microdroplet form (12) from a storage vessel, for example by means of a microdroplet jetting device (11). The substrate is temperature-controlled via a coolant (15), the surface to be jetted being located in a gas atmosphere or in vacuum (14). The substrate surface is maintained at a temperature T1 resulting in freezing of the impinging microdroplet, the substrate surface being possibly supportingly microstructured and comprising sensing elements. By controlled movement of either the substrate or the microdroplet jetting device the microdroplets can be applied singly and in patterns in arrays freely selectable or predetermined by the structuring of the substrate. The substrate with the applied microdroplets and the cells frozen therein are stored and/or processed by a processing means (17) ablating the material or applying said material at temperatures T2 of down to −273° C. In the cryogenic condition manipulations such as removal by mechanical ablation or addition of solutions or substances to the surface of the substrate can be undertaken. During thawing the substrate surface is brought to a temperature T1 above the freezing point of the enveloping solution and the microdroplet array thawed in a predefined manner.

30 Claims, 9 Drawing Sheets

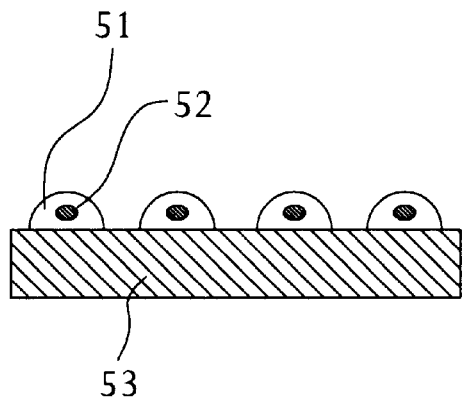
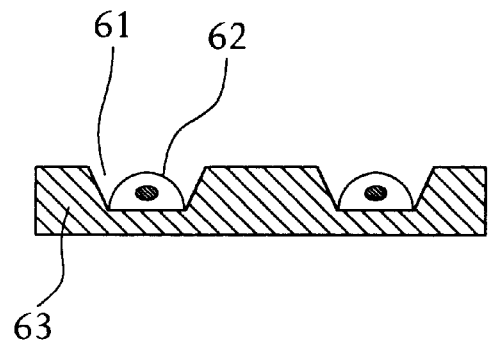
FIG. 5        FIG. 6
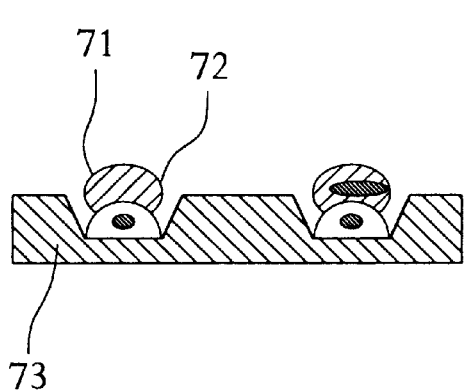
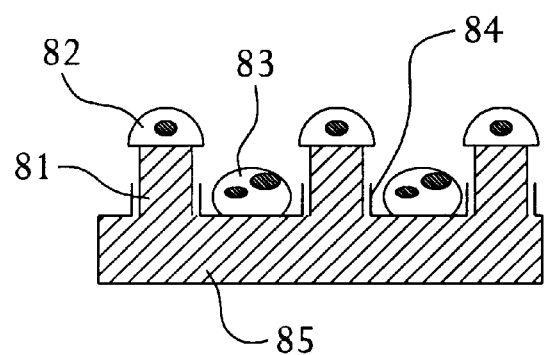
FIG. 7        FIG. 8

CRYOPRESERVING AND CRYOGENICALLY PROCESSING BIOLOGICAL OBJECTS

The invention relates to a method and an apparatus for cryopreserving microscopic objects, more particularly biological objects, single cells, cell formations or cell components or macromolecules fixated in accordance with predefinable temperature programs in two or three-dimensional patterns, changing these in the cryogenic condition and rethawing same with retention of cell vitality.

It has been common practice since decades in medical engineering, in setting up cell banks and in biological/pharmaceutical research to freeze cells and rethaw them according to given procedures without the living processes being irreversibly destroyed in at least part of the cryopreserved material. For this purpose the cells are mostly suspended in a solution and frozen in microtubes (R. Ian Freshney: "Tierische Zellkulturen", Walter de Gruyter 1990, page 221). The solutions are provided with substances which affect ice crystal formation (so-called cryopreservants such as e.g. dimethylsulfoxide, glycerine). These techniques have a proven record of success and result in survival rates of between a few percent and practically 100% when applied properly. Since in very many traditional applications the cell material after thawing first needs to be incorporated in a culture and strongly reproduced the survival rate following this kind of cryopreservation plays a minor role, this necessitating, however, that sufficient cells are available.

There is an increasing tendency for this no longer to be the case, however, in view of the methods in obtaining cells in medicine, genetics or molecular biology becoming more and more selective. One example is the designed genetic change of living cells which only produces the desired result in the case of few cells. By means of screening methods these cells are isolated and are available for further applications. One such application is hybridomas cell procurement (B. Gustafsson, "Cryopreservation of Hybridomas", in "Methods in Molecular Biology", Vol. 5, Eds. J. W. Pollard and J. M. Walker, 619–621) as is necessary and usual in the production of monoclonal antibodies e.g. for cancer therapy in which as a rule only very few cells from cell pairs (lymphocyte, myeloma cell) are formed and cryopreserved. It is especially in view of these low cell numbers as usual in this case that cryopreservation is possible only to a limited extent (R. Ian Freshney: "Tierische Zeilkulturen", Walter de Gruyter 1990, page 221) since major difficulties arise in handling the resulting small amounts of solution and reobtaining the cells. Furthermore, identifying cells individually by suspension techniques is not possible which, however, is necessitated by the aforementioned methods.

One particular drawback in freezing cells in cell suspensions is the gradient of the temperature distribution in the solution since the freezing conditions for the single cell are not known, or differ greatly due to their position in the suspension being undefined and failing to remain constant (M. J. Ashwood-Smith and J. Farrant, "Low Temperature Preservation in Medicine and Biology", Kent, England (1980)). Reproducing the conditions and thus standardization is, however, becoming more and more important for continuing work on cryopreserving single cells.

One modified kind of cryopreservation, especially for adhering cells is the preservation of cells grown on a surface (T. Ohno, "A simple method for in situ freezing of anchorage-dependent cells", in: A. Doyle, J. B. Griffiths, D. G. Newell, Cell and Tissue Culture, John Wiley & Sons, page 4C: 2.1). For this purpose, as a rule, thin cell layers, so-called cell monolayers are grown on suitable substrates (treated glass or plastic surfaces) and subsequently frozen and thawed as cell lawns. This method has the drawback that cell growth occurs randomly and a single cell in this case too, is difficult to be localized beyond the cryogenic time period. Since hitherto so-called microtiter plates have been used for growth, here too, no locally defined conditions can be achieved. On top of this the method is applicable only to cells growing adhered.

It is known, and employed in cryopreserving cells for electron microscopy (J. R. Harris, Electron Microscopy in Biology, IRL Press (1991)) that cells can be sprayed in microdroplets via nozzles into a strongly cooled atmosphere (H. Plattner, W. W. Schmitt-Fumian and L. Bachmann, "Cryofixation of single cells by spray-freezing", in E. L. Bendetti and P. Favard: "Freeze-etching, Techniques and Application", Soc. Franc. Microsc. Elecronique, Paris 1973, 81–100) and freeze very quickly by this technique (cooling rates of up to 10,000° C./s). This method has, however, the drawback that the cells drop into a storage vessel or a cryofluid with no defined positional relationship. A defined combination of cells and their individual identification is not possible.

In this arrangement microdroplet jetting devices may be used as are known e.g. in the case of printers for generating droplets of ink, or also for applying adhesives and other liquids to surfaces. Also known is the procedure of jetting cells in microdroplets and is put to use in cell sorting systems (M. R. Melamed, T. Lindmo and M. L. Mendelsohn (Eds.), "Flow Cytometry and Sorting", J. Wiley, New York (1990), 171–179). In this arrangement the cells are jetted individually in microdroplets, spatially sorted via a deflection device (e.g. electric fields) and collected in collecting vessels or applied to cell cultivation substrates. Here too, no individual manipulation of the objects is possible since largish amounts of cells (1,000 to 1,000,000 cells) are sorted in relatively large vessels.

BRIEF DESCRIPTION OF THE DRAWINGS

FIG. 5 is a schematic sectional view of a substrate without surface structuring with adhered microdroplets;

FIGS. 6–8 are schematical sectional views of substrates with structures with adhered microdroplets;

DETAILED DESCRIPTION

Figure 1:
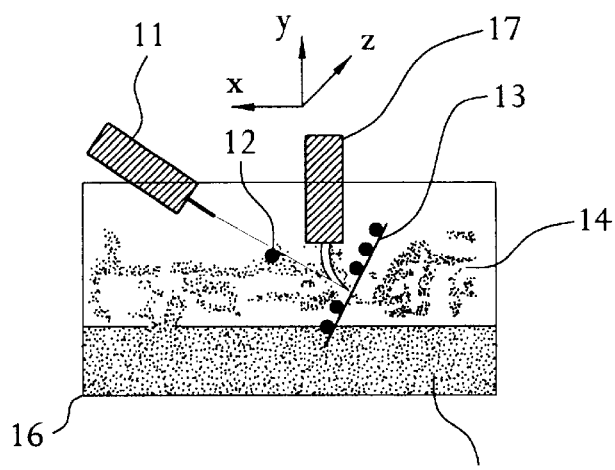
FIG. 1 is a sectional view of the configuration of an apparatus according to the invention.

With regard to the above prior art the present invention is based of the object of providing a method and an apparatus with allowing microscopic objects, more particularly biological objects, single cells, cell formations or components or macromolecular suspensions, to be freezed reproducibly, arranged and fixated, to be process and to be rethawed at a later time whilst retaining their vitality, it being intended to permit individual identification of the frozen and cryopreserved objects.

This object is achieved by the subject matters as set forth in the claims 1 and 17. Advantageous embodiments read from the dependent claims, these substantiating and expanding the abstract notion of defined fixation of biological objects in microdroplets on a temperature-controlled and, where applicable, microstructured substrate surface, modifying the surface layers or cells in the solid-state condition, their storage and later thawing, as circumscribed by the supporting features of claim 1 and 17.

The defined fixation of biological objects, being more particularly cells, may be achieved by shooting with a microdroplet jetting device or by positioning with a capillary or a carrier tip. In the latter case a microdroplet containing the biological object is attached to or generated at the tip, for example, of the capillary, the capillary or carrier tip being movable relative to the substrate surface with a controllable velocity profile.

The usages in accordance with the invention of the apparatus and method are set forth in claim 24.

By singling or grouping the microscopic objects contained in an enveloping solution or by apportioning the enveloping solution and thus encapsulating the objects or macromolecules or by apportioning the pure enveloping solution into microdroplets (picoliters up to a few microliters) in applying them to a substrate surface set to the temperature T1, which is controlled so that the microdroplets on impinging the substrate surface adhere and freeze in situ, the microscopic objects or macromolecules contained in the microdroplets are cryopreserved. Biological objects in this sense are understood to be more particularly single cells, cell formations or cell components. By selecting and specifically controlling the temperature T1 of the substrate cooling rates of a few ° C./min to a few thousand ° C./sec can be achieved for cooling the impinging microdroplets. By controlling in time and space the singling and application to the substrate surface well-defined fixations of the microdroplets and correspondingly the objects enclosed therein relative to each other and to the substrate can be achieved. Following application of the microdroplets the substrates can be brought via predetermined temperature profiles to a storage temperature T2 or processing temperature T3 which from experience is below –80° C., frequently in the range of –196° C. For brief storage and treatments higher storage temperatures are also possible which in each case are below the freezing point of the enveloping solution.

As an enveloping solution is understood principally any solution, mixed solution, serum or culture medium. Enveloping solutions for biological objects are required to ensure the vitality thereof, whereas for macromolecules all solutions and mixed solutions are feasible. In addition, it is required that, as far as encapsulated microscopic objects are concerned, any such type of object is meant whose dimensions are smaller than those of the microdroplet, i.e. including also more particularly liposomes, latex particles or other microparticles. Even enveloping solutions consisting of only one or several chemical components in the absence of the aforementioned objects are intended to come under the heading of the word object.

Temperature control of the substrate surface may preferably be done by means of a known cooling element (Peltier element) or by contact with cryogenic liquids (e.g. liquid nitrogen). The temperature of the jetted enveloping solution is intended to be in physiological ranges for biological objects.

One preferred apparatus for singling and applying biological objects are microdroplet jetting devices based more particularly on the principle of the piezoelectric effect, whereby by positioning the microdroplet jetting device and the substrate surface relative to each other freely selectable in space and time and controlling the singling and application process in time the microdroplets can be applied in the desired structures or positions on the substrate surface. By these microdroplet jetting devices microdroplets identical in size are produced which are substantial for reproducible and defined cryopreservation.

In a further embodiment transferring the enveloping solution and thus the encapsulated microscopic objects and macromolecules into aerosols (microdroplet cloud) by known spray methods is preferred, the aerosols being sprayed onto the cooled surface where they form thin and frozen layers. Here too, controlling application in time and space is possible.

Structuring in time and space is intended to be understood more particularly as a two or three-dimensional arrangement of the microdroplets on the substrate surface, whereby the microdroplets may be of the same or different enveloping solution and/or contain the same or different microscopic objects and macromolecules. By freezing the enveloping solution the technical teaching in accordance with the invention is suitable for producing three-dimensional structures of different biological objects, macromolecules or also only differing enveloping solutions reproducible, defined, fixated and orderly. This freedom of combination thus enables structures to be stably generated which could hitherto not be achieved. Due to thawing the structures applied to the substrate surface the various components of the structures can be caused to interact, whereby chemical reactions are able to sequence or biological objects caused to interact with each other or with the changed environment or also only thawing of biological material under conditions other than those of freezing may be achieved. Such asymmetries between freezing and thawing conditions occur in known cryomethods automatically in part but fail to permit being varied and reliably repeated as in the method as described here.

The substrate on which the microdroplets with the cells are applied may be made of glass, plastics, metal, semiconductor, ceramics or other material being consistent against temperature gradients. In the simplest case the substrate involved is a smooth, non-structured substrate to which the droplets are applied in a definable space from each other. Expediently, however, the surface of the substrate is structured to permit, on the one hand, the cells to be localized and retraced and, on the other, to support separating and selecting sensing of the cells or the freezing and thawing process. Useful in this context are especially substrates a few square millimetres up to a several square centimetres (e.g. semiconductor wafers, semiconductor chips) in size which have been structured by methods employed in semiconductor technology. Especially their good temperature conducting properties and the possibility of three-dimensional structuring in the micrometer and submicrometer range make silicon and its oxides as well as other semiconductor substrates a favorite, although also other metals and ceramics as the base material are favored.

Microstructuring in this sense is understood to be single, patterns or alternating sequences of recesses, channels, bridges, penetrations or protuberances in the substrate surface, whose dimensions as a rule correspond to the size of the cells or microdroplets or are executed finer or coarser. Typical dimensions for animal cells are 5 to 100 $\mu$m. In the case of bacteria, mycoplasma, viruses or similar small particles structurings are involved in the micrometer and submicrometer range.

In accordance with the invention these structures meet the following requirements:

- mechanical definition of the microdroplets relative to each other ( e.g. preventing droplet spreading); maintaining their individuality, among other things also as regards thawing in a liquid wetting the complete substrate surf ace, or also three-dimensional positioning for application of further microdroplets (with or without cell) at the location at which a predecessor droplet is located,
- installation of sensing elements, such as e.g. electrodes, optical and other sensors etc.,
- application of identification markings such as e.g. numbers, squares, lines etc. for observer orientation relative to the substrate surface,
- supporting elements for defined removal of frozen material or for applying further layers to the surface occupied by droplets; an example of which are walls between the rows of microdroplets exceeding or lower than the droplet height and up to the height of which frozen layers can be removed or applied by mechanical or other means of ablation,
- mounting the objects after thawing in a defined position (e.g. via electrical field cages generated by means of ultramicroelectrodes) or transporting objects to definable locations (in microchannels, by means of pumping systems),
- further use of the substrate as a complex measuring, metering or cultivating system before or after freezing or thawing so that it satisfies the function of a microlab; this being achievable by integration of usual semiconductor chips (containing pumps, sensors, active components such as FETs and LEDs) into the substrate surface directly or as a hybrid system or also by direct utilization of such semiconductor chips,
- modifying, destructing or building surface portions of the microdroplets after freezing (e.g. by laser ablation or jetting further microdroplets),
- establishing the hydrphobic/hydrophilic balance on the micrometer scale (e.g. by localized tenside coatings, amphoter coatings) or generating gradients or patterns on the surface,
- adapting to optical, spectroscopical or other measuring or evaluation units (e.g. as regards spatial dissolution, absorption properties),
- geometric standardization or automation of quantitative evaluation methods and their efficient technological and economic production (e.g. producing identical arrangements by masks),
- integrating elements permitting localization of microscopic objects, cells and microdroplets also in the cryogenic condition, including. their sensing; conceivable in this respect being fluorescent-marked structures which can also be rendered visible in ice and in the coolant, or electrode systems,
- installing elements permitting application of further substrates (structured or unstructured) or coverings as a sandwich structure of the frozen microdroplet structure.

In accordance with the invention it is possible at one or more cooling temperatures to modify the substrate to which microdroplets or cells have already been applied. Thus, simulant to cell droplet shooting, fluids may be applied via further microdroplet jetting systems to one and the same location, stacked or juxtaposed. This has the advantage that the solution composition, with which the cell comes into contact during freezing, is replaced during thawing by a solution having a totally different composition. By means of other methods of cell cryopreservation a corresponding asymmetry of the composition of the solution is not possible to this degree of variability and three-dimensionally.

Cooling the substrate to very low temperatures (<−100 to −273° C.) permits in addition the fastest freezing speeds attainable hitherto. Depending on droplet size and the deformation thereof on impinging the substrate surface as well as the structuring thereof cooling rates of a few to several thousand degrees/second can be achieved.

One particular advantage of corresponding substrates is their hot and cold sterilizability, where applicable, also their cleaning by means of ultrasound, guaranteeing sterile conditions as usual clinically.

One substantial aspect of the invention is patterning the distribution of microdroplets on the substrate surface and the microobject arrangements resulting therefrom. Thus, differing cells can be frozen in a small number, but also in a very high number directly juxtaposed, the interaction of which may not begin, however until after being thawed. The method and the apparatus are thus suitable for preparing medicinal/diagnostical as well as biotechnological/pharmaceutical test and sensor chips prior to their application and storing them over lengthy periods with no change to the fixation and retaining the vitality of the cells, and in dispatching them.

Using commercially available microdroplet jetting device, more particularly according to the piezoelectric principle, jetting frequencies can be produced up into the kHz range, thus making it possible to automate patterning and the target arrangement with computer control, as well as applying large cell counts (several million cells per second) quickly and precisely. Also conceivable, however, is deflecting the microdroplets by means of controllable electrode systems with a fast response, such as is already employed in e.g. electroprinting or in the cell sorting systems as already mentioned.

In addition the free accessibility of the microdroplets to the surface also makes it possible in the frozen condition to remove materials of the microdroplet or cells, to exchange such materials or also to supplement such materials by others (e.g. genetic material, enzymes, membrane materials etc.), this applying to both very small (micrometer, nanometer) regions and surface areas covering the complete microdroplet or the substrate. Also in this case, applying the material via a microdroplet jetting device may be involved. Furthermore, application from an aerosol or vapor phase, sputtering in a gas atmosphere or vacuum deposition on a target are also possible.

The ablation of frozen fluids may also be done in vacuum. This process can be done up to freeze drying and freeze etching.

For the purpose of mechanical stability or for achieving specific surface properties at interfaces ultrathin films may be applied to the substrate base on given surface layers prior to and after adjusting the temperature T1 (with or without microdroplets) so that miscible and/or non-miscible or demixed liquid zones materialize after thawing, meaning, apart from others, e.g. the change from hydrophilic to hydrophobic liquids, but also including thin contact layers, which produce the connection between thickly applied objects and the base droplet.

The method also permits application of several cell layers one on the other or insulated from each other by separating layers. On a substrate any number of differing media may be applied juxtaposed over a minimum surface area, thus enabling solution compositions to be tested in minute arrays, where necessary, also by subsequent application of substances in differing concentrations (e.g. on differing formulations). One application of these test systems is the screening of pharmaceuticals and pesticides or pollutants.

One substantial inventive aspect of the method is the shifting of a plurality of steps involved in the method into a temperature range extending from the freezing temperature of the enveloping solution down to almost absolute zero. This range enables materials (cytoplasma etc) which are usually fluid or semi-fluid in and around living Microsystems to be translated into a solid-state condition. By this measure manipulations on and in cells become possible which at physiological temperatures would automatically result in loss of vitality or which are impossible for time reasons. Translating the cells into the solid state condition permits substantial changes to be made to living systems practically without any time pressure and whilst retaining their vitality, this being termed "cryogenic cytosurgery" in the following.

Preferred example embodiments of the invention will now be detalned in the following with reference to the attached figures.

FIG. 1 is a sectional view showing the configuration of the apparatus schematically. From a microdroplet jetting device (11) single cells or a few cells each time are jetted with an enveloping solution (12) in microdroplets which through the gas phase impinge at high speed on the substrate surface (13). Due to a cryoliquid (15), present in a vessel (16) the substrate (13) is brought to a temperature T1 which as a rule lies far below the freezing point of the enveloping solvent. The substrate cooling arrangement is calibrated with the microdroplet jetting device (11) so that the microdroplets freeze adhesively on impinging the substrate surface (13) without the microdroplets bursting and substantially losing volume. The lower the temperature T1 is selected, the faster also the freezing action of the cell present in the droplet. In addition, this process can be further influenced via the microstructuring of the substrate surface (e.g. enlargening the surface area).

For droplet sizes (nutrient solution) of approx. 50 μm in diameter cooling to approx. -100° C. for a temperature T1=-196° C. is in the ms range and faster, thus enabling in cell cryopreservation almost all temperature programs, used hitherto, to be achieved by means of varying the substrate temperature T1, but also in varying the surface structure and properties (T conductivity), too.

To array the microdroplets, and thus also the cells to be preserved, either the substrate (13) and/or the microdroplet jetting device (11) are shifted relative to each other or, however, the microdroplets are deflected during their flight through the gas phase.

Following application of the microdroplets the substrate (13) is brought to a temperature T3 at which further processing is carried out, e.g. by means of a mechanical processing means (17) or at which storage is intended at temperature T2. As a rule this is the temperature of cryobanks as usually employed for cell storage (−80 to −273° C.).

On thawing, use can again be made of the apparatus modified as follows: instead of the coolant (15) the substrate (13) is brought either by a directly adhering device (thermistor or other local heat element) or via a warm fluid to a temperature T1 which as a rule lies above the freezing point of the enveloping solution. The heating process may be supported by jetting hot microdroplets from the microdroplet jetting device (11) (e.g. nutrient solution). However, also other means of heating may apply, up to microwaves, infrared (laser) radiation, or inductive heating of the substrate. This process too, can be completed in controllable phases, and where necessary, in a very short time.

The following FIGS. 2 to 16 show microscopic sections of the substrate surface. The dimensions of the structures illustrated amount to a few micrometers up to a few millimeters, preferably a few tens of micrometers. They may, however, also lie in the submicrometer range, e.g. for application with macromolecules.

Figure 2:
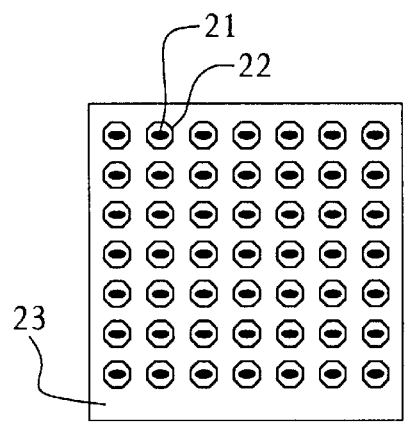
FIGS. 2–4 are schematical plan views of microdroplet arrangements on substrate surfaces.
Figure 3:
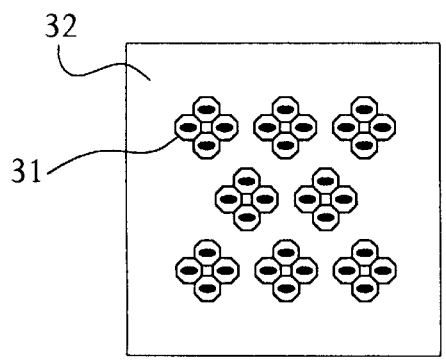
Figure 4:
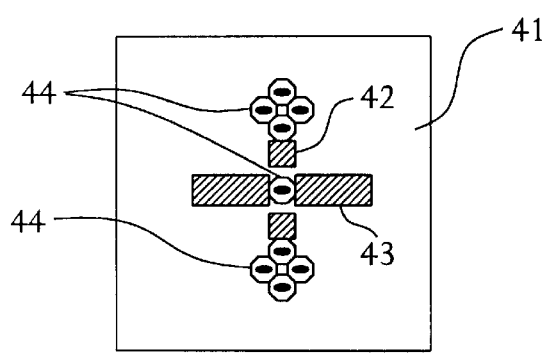

FIG. 2, FIG. 3 and FIG. 4 illustrate possible arrangements of microdroplets (22, 31, 44) on the substrate surface (23, 32, 41). FIG. 2 shows a square array of (7*7=49) microdroplets (22) in each of which a cell (21) is present. FIG. 3 shows an array of 8 assemblies of four microdroplets (31) each in contact with the other and in each of which a cell is present. FIG. 4 shows two assemblies of four and a single droplet (44) between structure elements (42, 43) serving sensing or mechanical definition. The elements identified (43) may be e.g. electrodes which also furnish measurement signals in the cryogenic condition. The elements identified (42) may be e.g. temperature sensors. The size of the elements illustrated is in the submicrometer and micrometer range.

FIG. 5 shows a substrate (53) in section without surface structuring, involving a substrate of glass, plastics, ceramic, semiconductor or metal material. Each of the jetted microdroplets (51) contains a cell, a cell organelle or a cell assembly (52). Depending on the temperature T1 selected the microdroplet is frozen in a form deviating from its original form. In accordance with the invention, following positioning of the microdroplets, a vacuum processing step is executed in which the substrate surface with the droplets is exposed to a vacuum selected so that the enveloping solvent is able to evaporate off or sublimate incrementally according to the temperature T1.

FIG. 6 shows a substrate (63) in section with microstructurings (roughly droplet-size depressions (61)) in each of which a microdroplet (62) has been jetted.

FIG. 7 shows an arrangement, as is described in FIG. 6 (substrate (73), microdroplet with cell (72)). Here, unlike the above situation, a second microdroplet (71) has been shooted to each microdroplet. This microdroplet (71) may contain a cell or it may also consist of another solvent. Depending on the depth of structuring o r on the temperature T1 selected two or more microdroplets may be placed, one on the other. Droplet columns of up to 50 droplets can be generated which in the frozen condition remain mechanically stable.

FIG. 8 shows a section through a heavily structured surface (85) in the depressions of which microdroplets with cells (83) are p resent between electrodes (84). On the webs (81) microdroplets having cells (82) of the same or different kind are likewise applied, e.g. in another solution. The basic configuration of this arrangement already corresponds to that of a prepared test chip as may be employed for screening pharmaceuticals or pollutants. It is no t until it has been thawed and a solvent wetting the whole surface area has been applied that the two kinds of cells come into contact or are activated. The cell-to-cell interactions are detected via the microelements (84).

Figure 9:
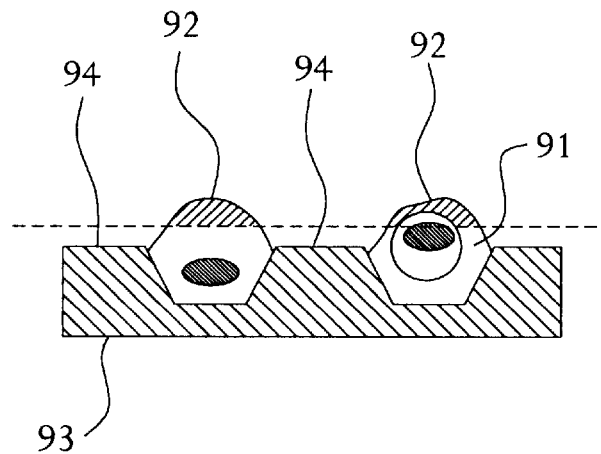
FIG. 9 is a schematical sectional view of a substrate with depressions and microdroplets protruding beyond the surface plane.

FIG. 9 shows the section through a substrate (93) with depressions bordered by berms of a defined height (94). These walls are so shallow that the microdroplets (91) protrude beyond the surface plane (indicated dashed) of the substrate (93) by a portion (92). The latter may be e.g. parted, milled or cut off by means of micromechanical devices (similar to a microtome) in the cryogenic condition or also ablated or blasted off with the aid of a laser beam, whereby it may be definitely desirable to also expose portions of the interior of the cell, to apply material (e.g. genetic material), to remove material (e.g. the cell core) and/or by further application e.g. lipides, polymers and the like to create the requirements for reclosing the cells during and after thawing, where applicable with retention of cell vitality. This method is, among others, to be considered as the starting point for cryogenic cytosurgery.

Figure 10:
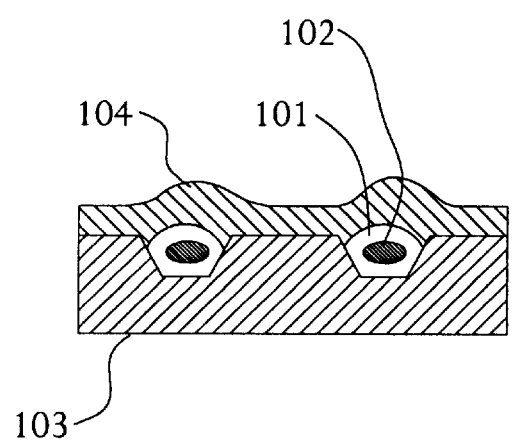
FIG. 10 is a schematical sectional view of a substrate with depression and microdroplets and an additional thin film.

FIG. 10 shows the section through a substrate (103) having depressions in each of which a microdroplet (101) including a cell (102) is present. This system is covered by a layer (104) which may comprise very thin films (of molecular dimensions) serving to physically stabilize the system, to influence the solvent composition during thawing, as a means of preventing evaporation or, however, to define an interface area (hydrophilic/hydrphobic). It may also be a material, however, with the aid of which, after thawing, the cells can be removed adhering to a thin film (104). Also conceivable are layers in the micrometer range.

Figure 11:
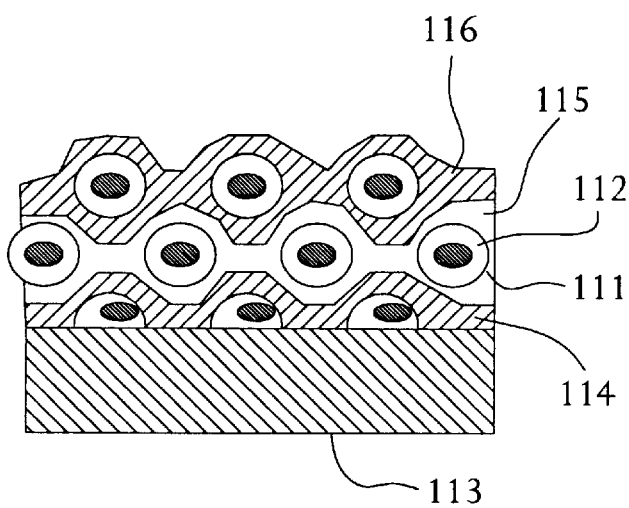
FIG. 11 is a schematical sectional view of a substrate with multilayers of microdroplets.

FIG. 11 shows the section through a substrate (113) on which layer-like microdroplets (111), each incorporating a cell, are applied and covered with layers (111, 115, 116), whereby the layers, microdroplets or cells may be of the same kind or different. This method serves e.g. the subsequent application of cryoprotectants for the thawing process. Since these substances frequently develop effects damaging to the cell and are not needed until thawed no interaction with the cell can occur in the cryogenic condition. In this way, high cell survival rates can be achieved.

Figure 12:
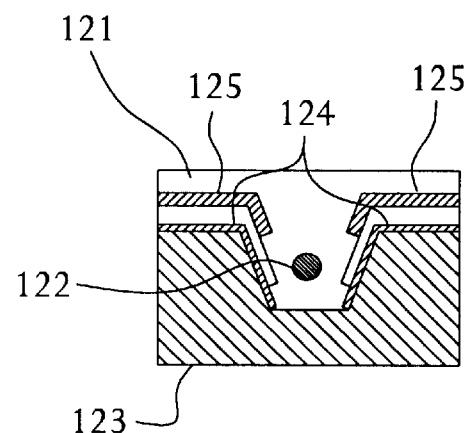
FIG. 12 is a schematical sectional view for a substrate with a depression being provided with a field cage.

FIG. 12 shows the section through a substrate (123) with a depression in which a microdroplet incorporating a cell (122) has been applied, after thawing. The cell (122) is levitated and, where necessary, sensed in a field cage in free solution (121) via electrodes (124) which are electrically insulated relative to each other via an insulating layer (125). After thawing, by using similar microelements the cells can be moved on the substrate or maintained in a defined position.

Figure 13A:
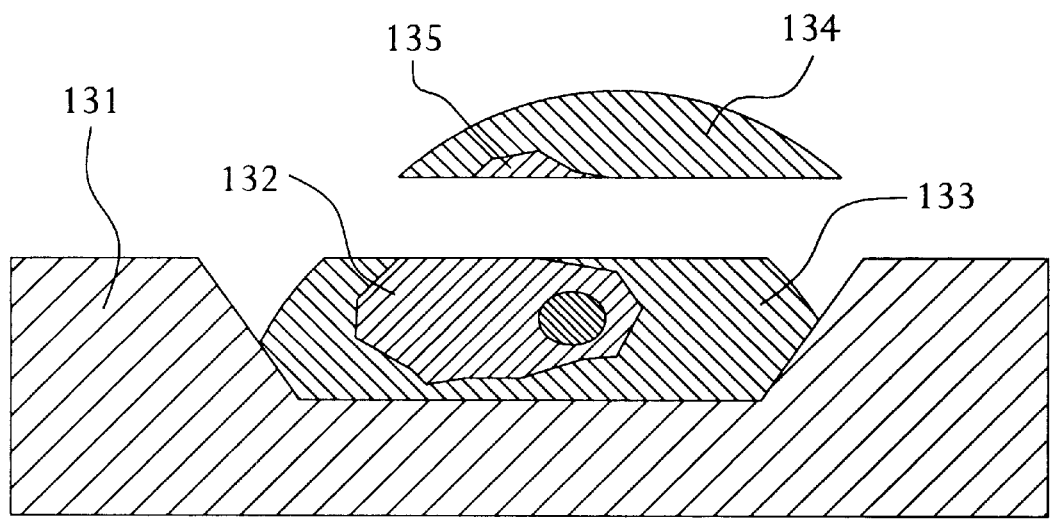
FIGS. 13a–13d, 14a–14d, 15a–15b, and 16-a–16b are schematical sectional views illustrating processing steps implemented according to the invention.
Figure 13B:
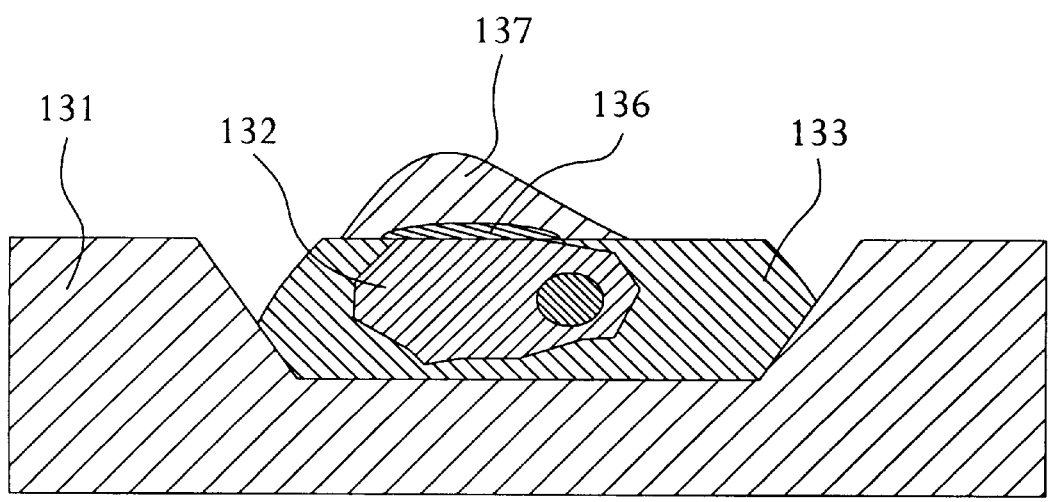

FIG. 13a shows in a magnified section representation a pit in a substrate (131) in which a microdroplet (133, 134) is present, in which a cell (132) is cryogenically preserved. At a suitable temperature below the freezing point of the enveloping solution and of the cell, where applicable, the cap of the droplet and part of the cell (134, 135) can be removed by a mechanical, or some other type of microcutter (plane grinding body). The cutting level is determined by the depth of the pit. The order of magnitude of the cutting surface area, for example, of a biological cell, may typically amount to a few $\mu m^2$. Also conceivable, however, are smaller openings, or openings in the range of 10 to 100 $\mu m^2$. In the simplest case the removed droplet cap is scrapped and one or more thin layers is applied to the surface of the cut, as illustrated in FIG. 13b. The surface of the cell is covered, slightly beyond the definition thereof, with a solution (136) which may exhibit e.g. lipophilic properties or correspond to a lipid bilayer or multilayer. It is likewise possible to apply thin films of corresponding substances localized or covering a broad surface area as a tight seal. To further stabilize the sequence of layers during thawing further layers (137), e.g. also in a hydrophilic/hydrophobic sequence may be applied. Applying the layers and solutions may be brought about by means of the microdroplet jetting device already described, but also by nebulizing, deposition from the gas phase etc. In this way adequate dosage and partial coverage is assured. On thawing, stabilization of the interfaces occurs via the interaction or penetration of the layers as well as via staggering the thawing temperatures so that the cells opened previously physically are closed off, whilst retaining their vitality.

Figure 13C:
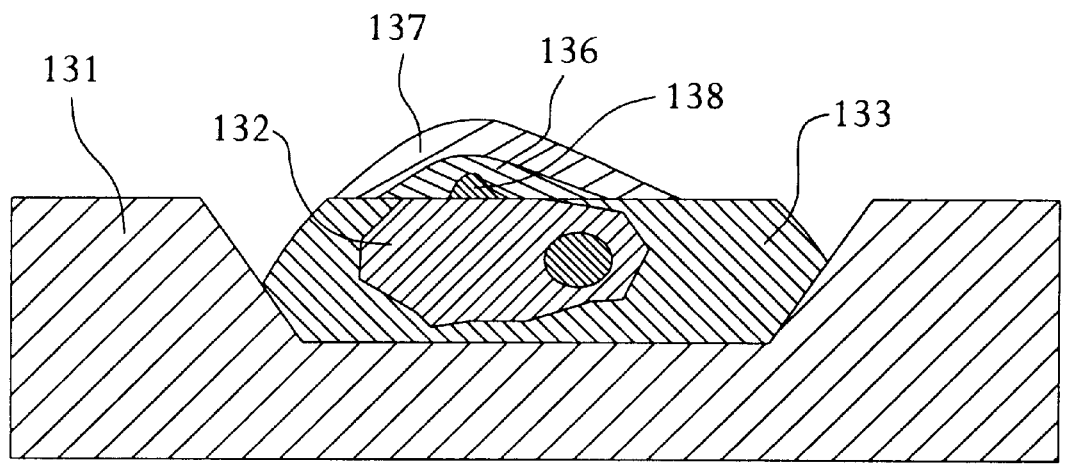

In FIG. 13c, in addition to the layers (136, 137) cited in FIG. 13b, a microdroplet (138) has previously been applied to the opened cell surface or brought into the vicinity thereof, containing a substance intended to gain access to the metabolism of the cell. This substance may be genetic material, macromolecules, marker substances, isotopes or also artificial bodies.

Figure 13D:
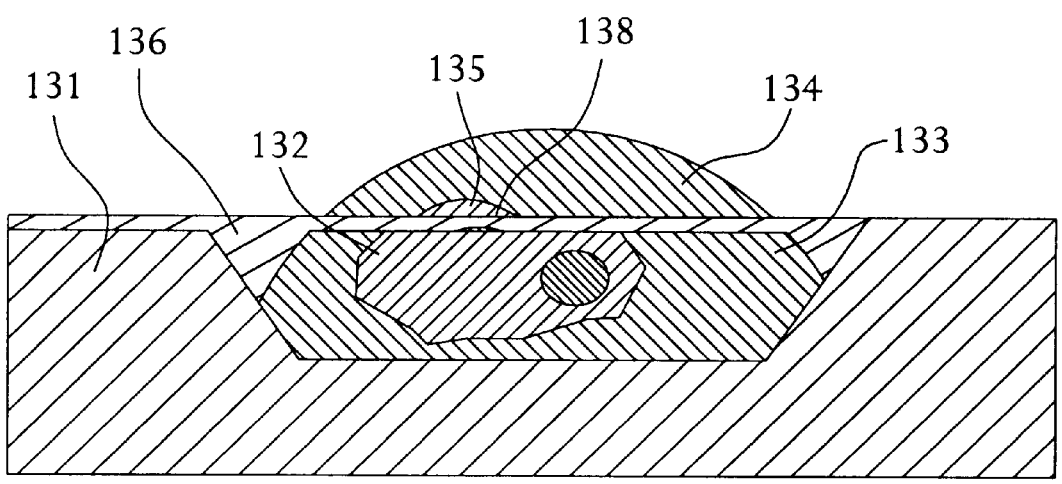

FIG. 13d shows the application of a solvent droplet (138) as described in FIG. 13c, after which the complete surface of the substrate is covered with a solution (136) which freezes in place and on thawing produces the orderly connection to the cell cap (135) subsequently applied and the original portion of the microdroplet (134). All steps are done in the frozen condition, whereby as a rule temperatures of below −80° C. are expedient since then no further migratory growth of ice crystals occurs.

Figure 14A:
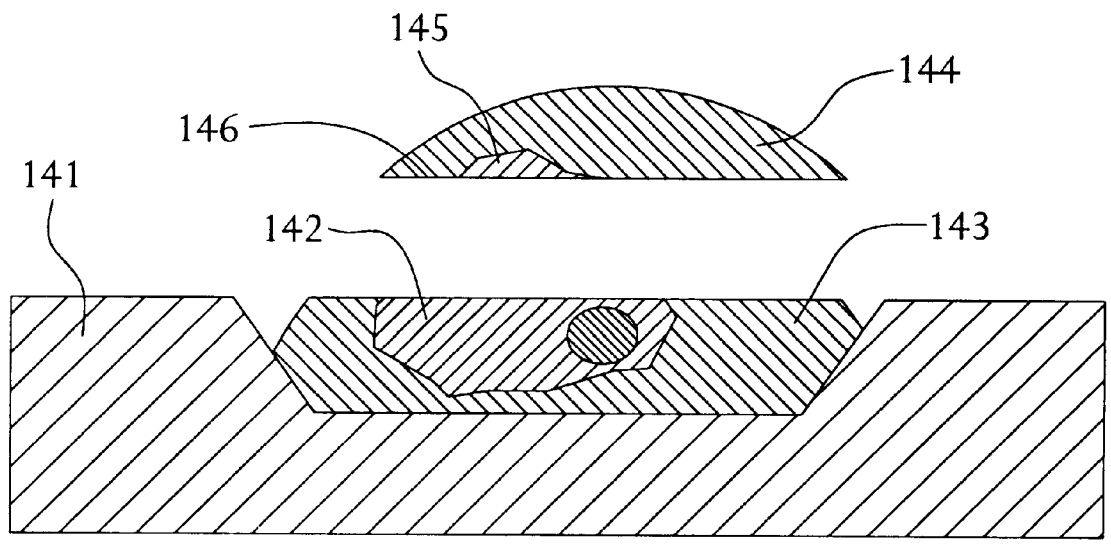
Figure 14B:
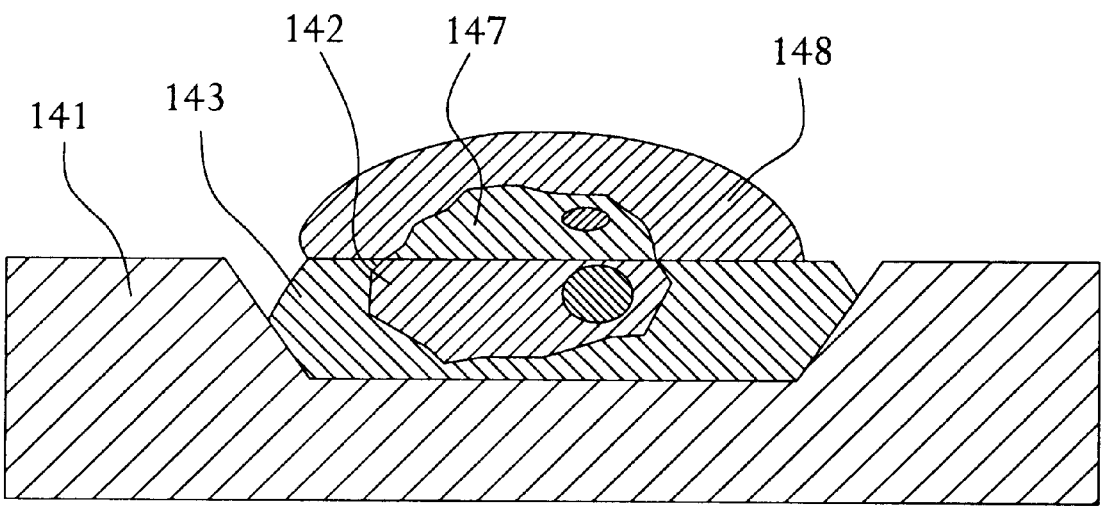

In FIG. 14a ablating a major portion (144) of a microdroplet (143) frozen in place and of the cell (142, 145) present therein is shown. The cutting level is dictated by the height of the berm (141), also the cell wall and membrane (145) being parted microscopically fine. Unlike the situation shown in FIG. 13 in this case, however, the ablated portion (144, 145, 146) is not scrapped but further used for placement on another microdroplet having been similarly treated. The result of such a manipulation of two cell portions (142, 147) and droplet portions (143, 148) is shown by FIG. 14b in section. For a better amalgamation of both portions it may be necessary to apply further layers to the connecting surface areas of both microdroplets prior to placement which bring about closure of any possibly remaining openings (not shown). The elliptical circles in the cells depict cell organelles.

Figure 14C:
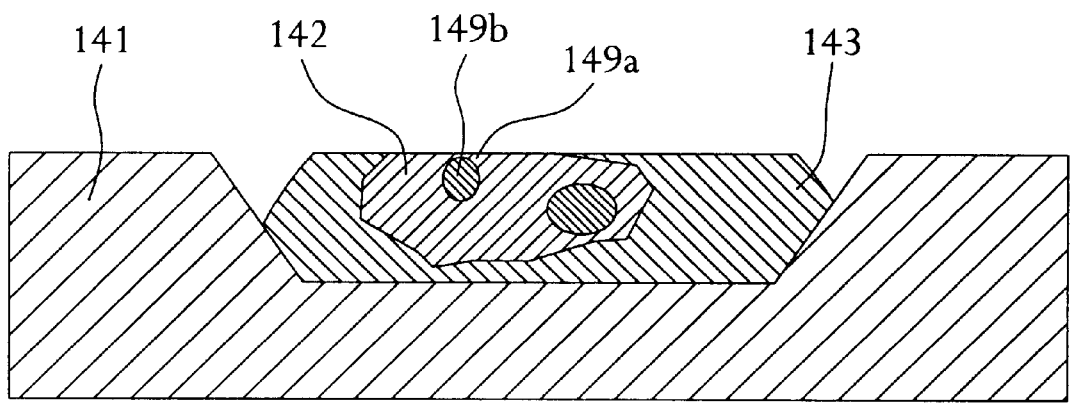
Figure 14D:
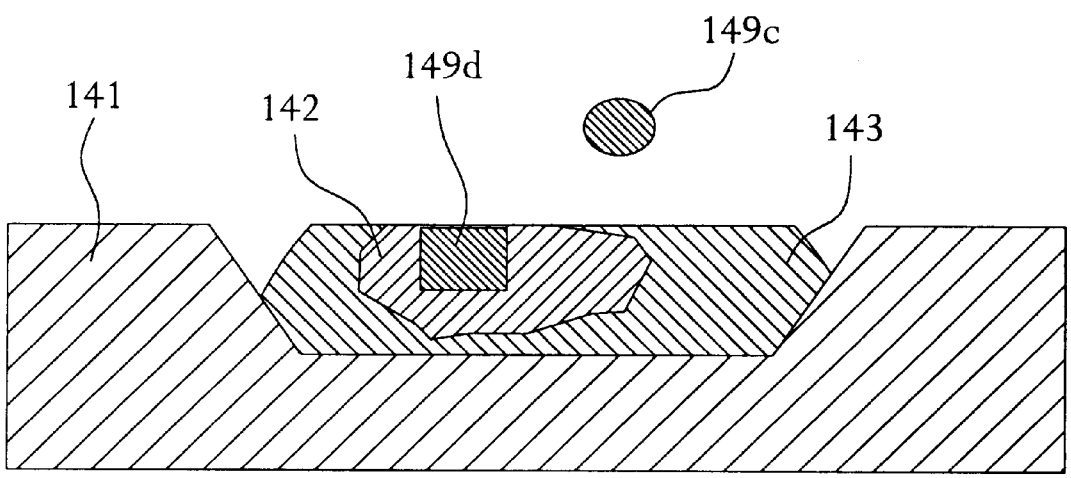

FIGS. 14c and d illustrate two further types of manipulation relevant to cell-biological and medical procedures, namely, in the one case, removing a microvolume (149a) from the cell material and inserting an organelle, an artificial body or other cell ompartiment (149b), and, in the other, removing a cell compartment (illustrated in this case as removal of the cell core (149c)) and replacing the removed volume by a foreign substance (149d) which as a rule should be physiologically compatible or which may also be of some other cellular origin. This may also involve, however, a solid particle, or a gas space tolerated by the cell interior after thawing. Areas of application of these methods of manipulation are genetics, molecular biology, biotechnology and medicine.

Figure 15A:
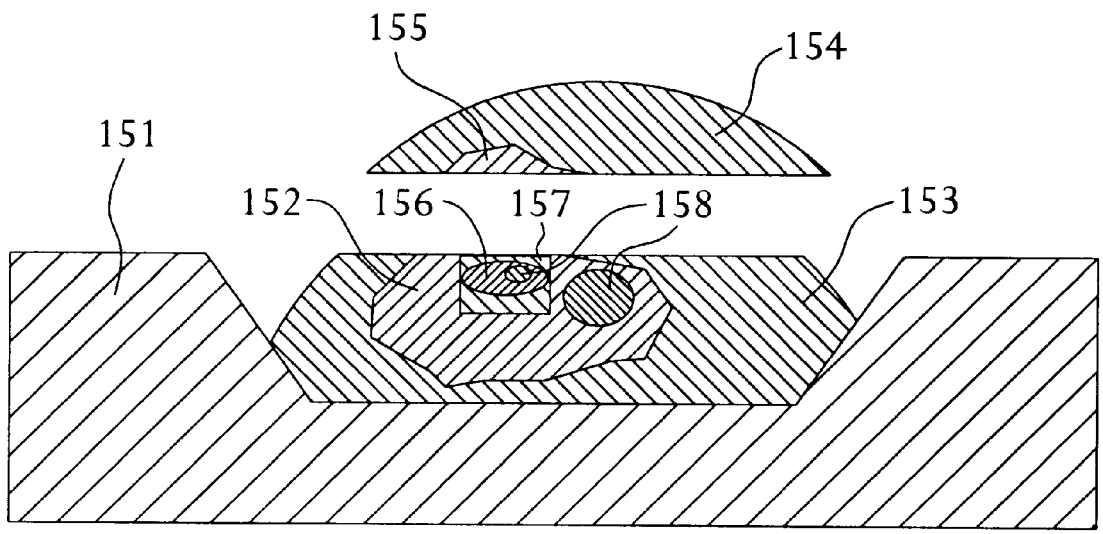

FIG. 15a illustrates opening a cell, as already described, removing a portion of the cell material and inserting another material (157) and a complete cell (156), e.g. a cell of bacteria, single-cell algae. Here, (158) identifies the cell organelles, (152) the cell body, (153) the droplet portion on the substrate, (151) the berm on the substrate and (155) the ablated cell portion, and (154) the ablated droplet portion.

Figure 15B:
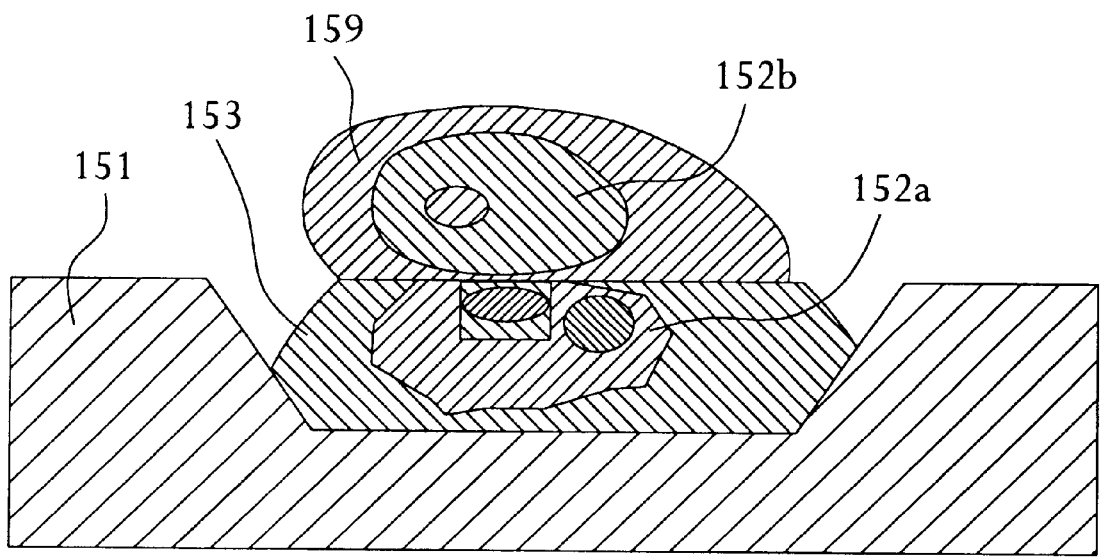

It is evident from FIG. 15b that the infringement and contact surface area between two droplet portions (153, 159) and cell portions (152, 152b) placed one on the other in this way may be a very small surface area (in the micrometer or even submicrometer range). The object of this manipulation is to form a cell pair, a cell fusionate (after thawing), or a temporary or permanent cell connection, the applications of which lie mainly in hybridoma engineering.

Figure 16A:
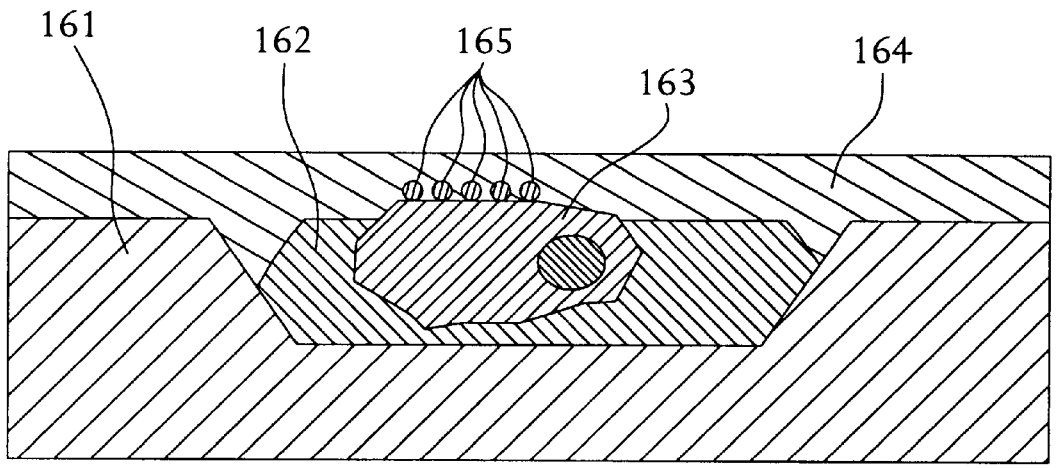

FIG. 16a illustrates in a section view the result of the following method steps:

Droplet material (162) is removed from above the substrate (161) in the way as already described, without, however, exposing or infringing the cell surface. On the exposed surface area of the cell (163) materials (165) are applied localized in microdosages, e.g. by defined microdroplet jetting and instant freezing. These materials may contain genetic molecules, binding proteins, enzymes, marker molecules, salts etc which during and following thawing become attached or bonded to the surface or are intended to gain access to the cell or in regions in the vicinity of the wall. To stabilize and support the thawing process it may be necessary to apply further layers (identified in this case by (164)) also in greater thickness. With these steps in the method too, a medical, biotechnological or environmentally sorted technical application is intended. Thus, the cell may be present in a sensor chip in testing for the influence of environmental noxious elements after thawing pursued by measuring the cell parameters. In this context it should again be noted that the cited processes may also be supported by cavities generated by bridging via the droplet material or cell.

Figure 16B:
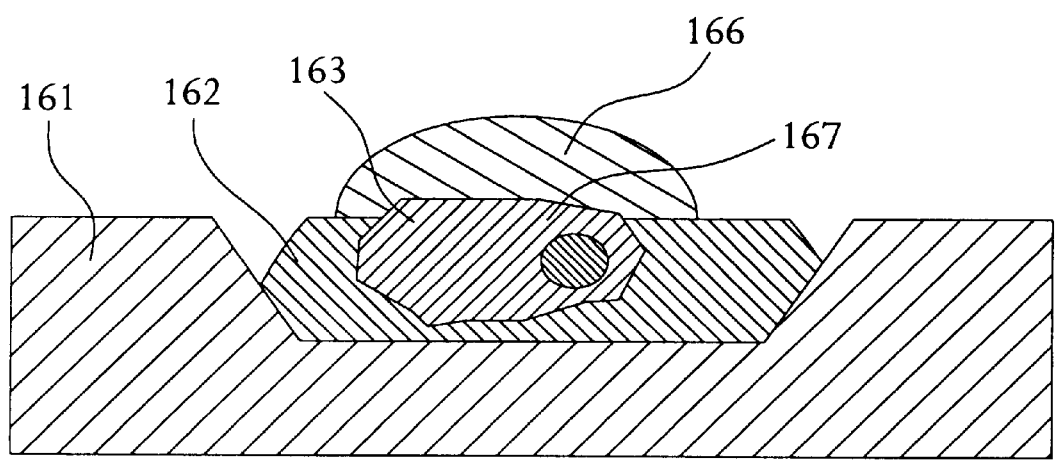

FIG. 16b depicts a further step in the method of processing a microdroplet (162) and the cell (163) present therein cryogenically freezed. Here, use is made of the fact that a liquid droplet (166) employed in jetting the cryogenic droplet or cell material does not freeze without briefly liquifying part of the frozen material (163, 162) on which it impinges. How large this material region (167) is, depends on the substrate temperature as well as on the droplet temperature and the volumes of both microdroplets. At very low temperatures of the substrate and temperature control of the microdroplet (166) in the vicinity of the freezing point, the thawing region (167) is molecular in dimension, whereas at substrate temperatures somewhat below the freezing point and high microdroplet temperatures, in the case of aqueous solutions up to 100° C., the dimensions are microscopic up to the substrate surface. Both are made use of to bring about in a defined way mixed phases, molecular and microscopic restructurings or bonding processes on the substrate surface.

The steps in the method and apparatuses explained by way of biological objects as an example may likewise find application in the field of microtopographic, multicompartmented reaction chemistry.

We claim:

1. A method of cryopreserving and cryogenically treating microscopic biological objects comprising cell formations, single cells, cell components or macromolecules on substrate surfaces, the method comprising the steps of:

introducing said objects into at last one storage reservoir including an enveloping solution, guiding said enveloped objects from said at least one storage reservoir to said substrate surface being temperature controllable and having a temperature T1, and fixedly adhering said objects to said substrate surface, wherein during said guiding said objects are surrounded by said enveloping solution so that microdroplets are formed whereby said guiding is obtained by means of at least one microdroplet placement means being adapted to control the movement of said microdroplets in time and position, wherein said microdroplet placement means is a microdroplet jetting device and said guiding of said objects is done by changing the orientation of the microdroplet movement from shot to shot relative to the substrate surface and/or movement of said substrate surface relative to the microdroplet jetting device such that said objects adhere to said surface in defined spacings or in patterns, after said adhering the target temperature is adjusted to a preservation temperature T2 or a processing temperature T3 and said loaded substrate surface is stored and/or processed, and said temperature T1 lies above the freezing point of water and the temperatures T2 and T3 are in the range of −2° C. to −273° C.

2. A method of cryopreserving and cryogenically treating microscopic biological objects comprising cell formations, single cells, cell components or macromolecules on substrate surfaces comprising the steps of:

introducing said objects into at least one storage reservoir including an enveloping solution, guiding said enveloped objects from said at least one storage reservoir to said substrate surface being temperature controllable and having a temperature T1, and fixedly adhering said objects to said substrate surface, wherein during said guiding said objects are surrounded by said enveloping solution so that microdroplets are formed whereby said guiding is obtained by means of at least one microdroplet placement means being adapted to control the movement of said microdroplets in time and position, wherein said microdroplet placement means is a microdroplet jetting device, and said guiding of said objects is done by changing the orientation of the microdroplet movement from shot to shot relative to the substrate surface and/or movement of said substrate surface relative to the microdroplet jetting device such that said objects adhere to said surface in defined spacings or in patterns, after said adhering the target temperature is adjusted to a preservation temperature T2 or a processing T3 and said loaded substrate is stored and/or processed, and said temperatures T1, T2 and T3 are in a range of −5° C. to −273° C.

3. The method as set forth in claim 1, wherein one or more substrates surface zones are jetted with objects simultaneously or in sequence by a plurality of microdroplet jetting devices.

4. The method as set forth in claim 1, wherein prior to loading the substrate, the substrate surface is coated by a microdroplet jetting device partially or totally with a gel, a molecular layer, a liquid or a polymer or with a plurality or combination thereof.

5. The method as set forth in claim 1 or 2, wherein said objects and microdroplets during flight to said substrate surface are sensed optically or electrically, the impinging position of said microdroplets with said objects being variable depending on the data obtained by sensing.

6. The method as set forth in claim 1 or 2, wherein said storing and/or processing of said loaded substrate surface is made in liquid nitrogen or similar cryoliquids or the gas phases thereof.

7. The method as set forth in claim 1 or 2, wherein the complete method or also individual working steps thereof is/are carried out at pressures deviating from normal pressure.

8. The method as set forth in claim 1 or 2, wherein prior to storing and/or processing said loaded substrate surface is coated with further thin layers, said thin layers being formed by a frozen solution applied by a microdroplet jetting device or generated by nebulizing, sputtering in a gas phase or vacuum deposition.

9. The method as set forth in claim 8, wherein said thin layers are metallic layers.

10. The method as set forth in claim 1 or 2, wherein several microdroplets with or without cells, of the same or differing composition, are cryogenically fixed by one on the other or juxtaposed.

11. The method as set forth in claim 1 or 2, wherein for storing and/or processing a layer is applied to said substrate surface, said layer allowing an ablation of said microdroplets including said cells or portions thereof in a fixed condition.

12. The method as set forth in claim 1 or 2, wherein prior to being frozen in place and/or following thawing by heating said substrate surface up to a temperature above the freezing point of said enveloping solution, said cells are manipulated via electrical field forces or maintain suspended in said enveloping solution.

13. A method of cryogenically treating microscopic biological objects comprising cell formations, single cells, cell components or macromolecules on substrate surfaces, comprising the steps of:
    guiding said objects with an enveloping solution as microdroplets to said substrate surface,
    fixedly adhering said objects on said substrate surface in a freezed condition, and
    processing said objects including a removal of object material, wherein said guiding of said microdroplets with said objects is conducted by a microdroplet getting device, and said guiding of said objects is done by changing the orientation of the microdroplet movement from shot to shot relative to the substrate surface and/or movement of said substrate surface relative to the microdroplet jetting device such that said objects adhere to said surface in defined spacings or patterns.

14. The method as set forth in claim 13, wherein said objects are biological cells or cell formations or cell components and the processing includes a removal of cell material.

15. The method as set forth in claim 13, wherein said removal or a degradation of material is a mechanical removal and an optical ablation, a freezed etching and/or an evaporation in vacuum.

16. The method as set forth in claim 13, comprising a further step wherein additional material is applied and whereby the said additional material is of synthetic, genetic or cellular origin, or said additional material is adapted to a closing of the open cells, during or after thawing whilst retaining vitality thereof.

17. The method as set forth in claim 13, wherein said fixed adhering is obtained by a method according to claim 1 or 2.

18. An apparatus for cryopreserving and cryogenically processing microscopic biological objects comprising cell formations, single cells, cell components or macromolecules on substrate surfaces wherein
    a microdroplet jetting device for jetting controlled in time and in position droplets of an enveloping solution including said objects enveloped thereby on a temperature controlled substrate surface, said substrate surface during said jetting has a temperature T1 above the freezing point of water and after said jetting temperatures T2 or T3 in the range of $-2°$ C. to $-273°$ C., said microdroplet jetting device being adapted to change the orientation of the microdroplet movement from shot to shot relative to the substrate surface and/or said substrate surface being adapted to be moved relative to the microdroplet jetting device.

19. An apparatus for cryopreserving and cryogenically processing microscopic biological objects comprising cell formations, single cells, cell components or macromolecules on substrate surfaces wherein
    a microdroplet jetting device for jetting controlled in time and in position droplets of an enveloping solution including said objects enveloped thereby on a temperature controlled substrate surface, said substrate surface during and after said jetting has a temperature in the range of $-5°$ C. to $-273°$ C., said microdroplet jetting device being adapted to change the orientation of the microdroplet movement from shot to shot relative to the substrate surface and/or said substrate surface being adapted to be moved relative to the microdroplet jetting device.

20. The apparatus as set forth in claim 18 or 19, wherein said apparatus contains processing means for storing and/or or manipulating said applied objects.

21. The apparatus as set forth in claim 18 or 19, wherein said substrate surface has a surface structure containing more particularly microelectrodes, electronics sensing elements or components, depressions, protuberances, penetrations or passages or fine structures such as ripples, columns, tips, berms which enlarge said surface with dimensions typically in the micrometer or submicrometer range.

22. The apparatus as set forth in claim 18 or 19, wherein said microdroplet jetting device and/or substrate surface consist of a semiconductor material, more particularly based on silicon.

23. The apparatus as set forth in claim 18 or 19, wherein said substrate surface is coolable or heatable according to time-defined temperature programs.

24. The apparatus as set forth in claim 18 or 19, wherein said substrate surface is coolable or heatable according to time-defined temperature programs, further wherein said substrate surface is coolable by a coolant bath containing liquid nitrogen or by the gas atmosphere of said cooling bath.

25. The apparatus as set forth in claim 18 or 19, wherein said substrate temperature and said droplet temperature can be adjusted independently of each other and for the microdroplets to be jetted may also lie far above the freezing point of the droplet solution.

26. An apparatus for cryogenically processing microscopic biological objects comprising cell formations, single cells, cell components or macromolecules on substrate surfaces comprising
    means for guiding said objects with an enveloping solution as microdroplets to said substrate surface, wherein said means for guiding is a microdroplet jetting device,
    means for adjusting the substrate temperature so that the objects are fixedly adhered in a freezed condition on said substrate surface, and
    processing means being adapted to remove object material, said microdroplet jetting device being adapted to change the orientation of the microdroplet movement from shot to shot relative to the substrate surface and/or said substrate surface being adapted to be moved relative to the microdroplet getting device.

27. The apparatus as set forth in claim 26, wherein said processing means comprises a microtome cutter, microdrilling and milling machine, a laser beam or some other element with which material can be removed or ablated mechanically, thermally or optically in a cryogenic condition.

28. Use of the method as set forth in claim 1 or 2 for cryopreserving cells for a cell bank usable for medical, biological, pharmaceutical or other purposes or for producing substrates as test chips, sensors, screening elements in medical diagnosis, environmental engineering and pharmaceutical research.

29. Use of the method set forth in claim 13 for cryopreserving cells for a cell bank usable for medical, biological, pharmaceutical or other purposes or for producing substrates as test chips, sensors, screening elements in medical diagnosis, environmental engineering and pharmaceutical research.

30. Use of the apparatus set forth in claim 18 or 19 for cryopreserving cells for a cell bank usable for medical, biological, pharmaceutical or other purposes or for producing substrates as test chips, sensors, screening elements in medical diagnosis, environmental engineering and pharmaceutical research.

* * * * *